United States Patent
Kroll

[19]

[11] Patent Number: 5,988,161
[45] Date of Patent: Nov. 23, 1999

[54] ALTITUDE ADJUSTMENT METHOD AND APPARATUS

[76] Inventor: Mark W. Kroll, 651 Carnellon Ct., Simi Valley, Calif. 93065

[21] Appl. No.: 08/927,242

[22] Filed: Sep. 11, 1997

[51] Int. Cl.[6] .................................................. A61G 10/00
[52] U.S. Cl. ............................... 128/202.12; 128/203.25; 128/205.11
[58] Field of Search ......................... 128/202.12, 203.25, 128/205.11, 205.24, 205.25, 205.26

[56] References Cited

U.S. PATENT DOCUMENTS

| | | |
|---|---|---|
| 5,101,819 | 4/1992 | Lane et al. . |
| 5,398,678 | 3/1995 | Gamow et al. . |
| 5,647,345 | 7/1997 | Saul .................................. 128/201.23 |
| 5,799,652 | 9/1998 | Kotliar .............................. 128/205.11 |
| 5,848,589 | 12/1998 | Welnetz ............................. 128/202.12 |
| 5,850,833 | 12/1998 | Kotliar ............................... 128/202.12 |

FOREIGN PATENT DOCUMENTS

| | | | |
|---|---|---|---|
| 1456161 | 2/1989 | U.S.S.R. ........................... 128/205.11 |
| 1531986 | 12/1989 | U.S.S.R. ........................... 128/205.11 |
| 1602543 | 10/1990 | U.S.S.R. ........................... 128/205.11 |
| 1674858 | 9/1991 | U.S.S.R. ........................... 128/200.24 |
| 1680166 | 9/1994 | U.S.S.R. ........................... 128/202.12 |

*Primary Examiner*—Aaron J. Lewis

[57] ABSTRACT

A method and apparatus for allowing an individual to adjust to high altitudes is taught. The invention teaches the use of a small portable breathing gas control system to adjust the gas concentrations going to the subject's mask. This allows the subject to gradually adjust to high altitudes by breathing through this system during sleeping or other quiet activities.

19 Claims, 5 Drawing Sheets

ALTITUDE ADJUSTMENT METHOD AND APPARATUS

BACKGROUND OF THE INVENTION

Altitude sickness strikes thousands of individuals every year resulting in problems from sleep disorders to pulmonary edemas to death. These individuals are skiers, mountain climbers, or merely business travelers to high altitude regions. The key to dealing with the altitude sickness is taking advantage of the body's ability to gradually acclimatize through a transition through progressively higher altitudes.

Unfortunately, most individuals do not have the time to acclimatize. For example, an individual flying to a high ski hill will typically spend a few hours of flying and driving to be at the ski hill thus depriving the body of the opportunity to acclimatize.

The physiology of altitude sickness and the adjustment to altitude is covered in numerous textbooks. An excellent one is "Medicine For Mountaineering" by James Wilkerson, M.D. Copyright 1992, published by The Mountaineers of Seattle, Wash. from which the immediately following discussion is liberally taken.

The body adjusts to altitude by increasing respiratory volume, increasing the pulmonary artery pressure, increasing the cardiac output, increasing the number of red blood cells, increasing the oxygen carrying capability of the red blood cells, and even changing body tissues to promote normal function at lower oxygen levels.

At an altitude level of 3,000 feet the body already begins increasing the depth and rate of respiration. As a result of this more oxygen is delivered to the lungs.

In addition, the pulmonary artery pressure is increased which opens up portions of the lung which are normally not used, thus increasing the capacity of the lungs to absorb oxygen. For the first week or so, the cardiac output increases to increase the level of oxygen delivered to the tissues. However, that particular adjustment fades after the first week.

The body also begins to increase the production of red blood cells. Other changes include the increase of an enzyme (DPG) which facilitates the release of oxygen from the blood and increase the numbers of capillaries within the muscle to better facilitate the exchange of blood with the muscle.

About 80% of the adaptation is finished by 10 days.

Slowly increasing the altitude from sea level to the target altitude appears to be the best solution.

The most difficult time for altitude sickness sufferers is evening when the primary the function is sleeping. This is most likely due to the fact that the breathing rate decreases during sleep and thus the coping mechanism of increased respiratory rate is somewhat thwarted.

Gamow (U.S. Pat. No. 5,398,678) teaches a portable chamber to facilitate the function of an individual at higher altitudes by increasing the pressure within the chamber above that of the ambient. Lane (U.S. Pat. No. 5,101,819) teaches a method of introducing nitrogen into a flight training hypobaric chamber to simulate the lower oxygen concentrations at higher altitudes for fighter pilots.

The inventor is not aware of any other art that discusses the use of a portable device for helping an individual to adjust to deal with altitudes.

DETAILED DESCRIPTION

Figure 1:
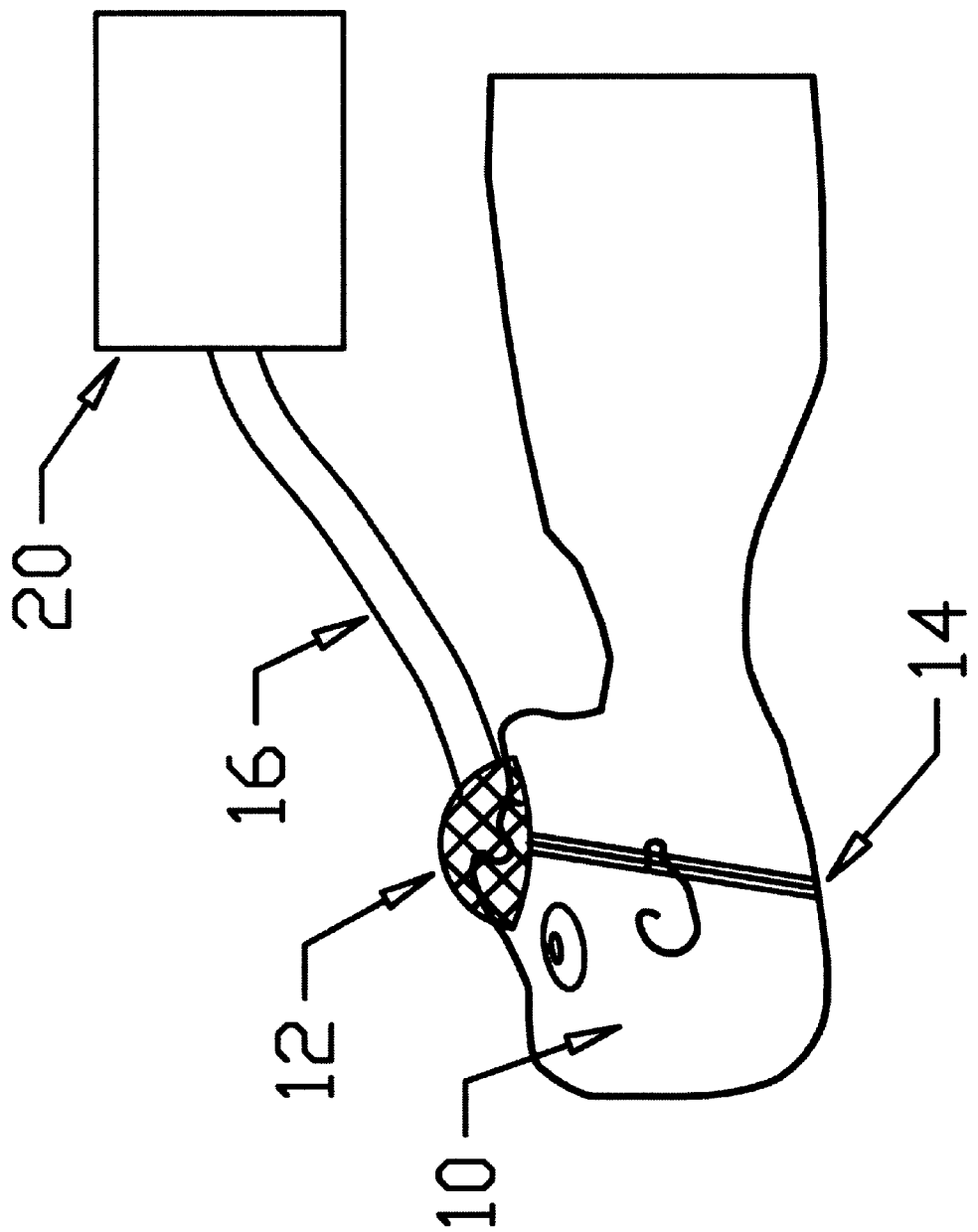
FIG. 1 shows a subject at rest using the device.

FIG. 1 shows a subject 10 using the device with mask 12 over the nose and mouth secured around the head by strap 14. The mask communicates with the main exchange unit 20 through hose 16. For convenience, hose 16 should be long enough so that the exchange unit 20 can be far enough away from the patients so that it does not interfere with their sleep. However, for optimal performance in air mixing, the hose could be made shorter to allow for more shallow breaths for the appropriate gas levels. Alternatively, the exchange unit could be made very small and built into the mask thus obviating the hose 16.

Figure 2:
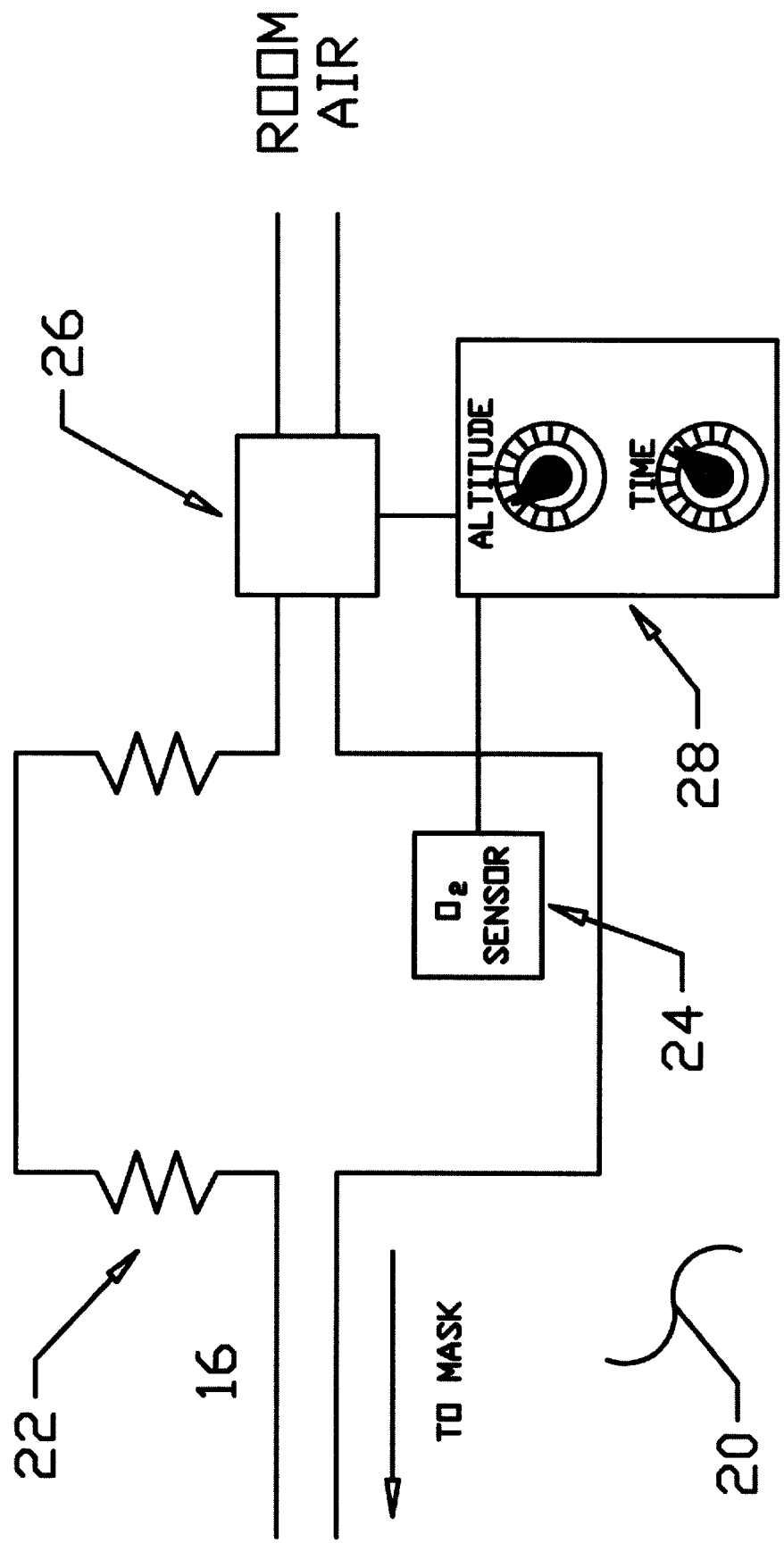
FIG. 2 shows a simple embodiment of the device.

FIG. 2 shows the details of the exchange unit 20 beginning with the hose 16 going to the mask. Flexible sides 22 allow for the chamber to expand and contract. Alternatively, flexibility could be gained by the use of elastic polymers or other materials for the unit surfaces.

Oxygen sensor 24 sits inside the chamber and feeds its signal to a control unit 28. The control unit 28 has a setting for an altitude and time. The control unit then controls the room air solenoid 26 to allow the passage of room air into the exchange unit when necessary.

The basic operation is rather straightforward. The oxygen sensor monitors the oxygen and controls the room air solenoid. The solenoid would be open or closed depending upon whether the internal oxygen level is at that appropriate level desired for the altitude simulation.

More details of this are given in the discussion of the methods which are following.

Figure 3:
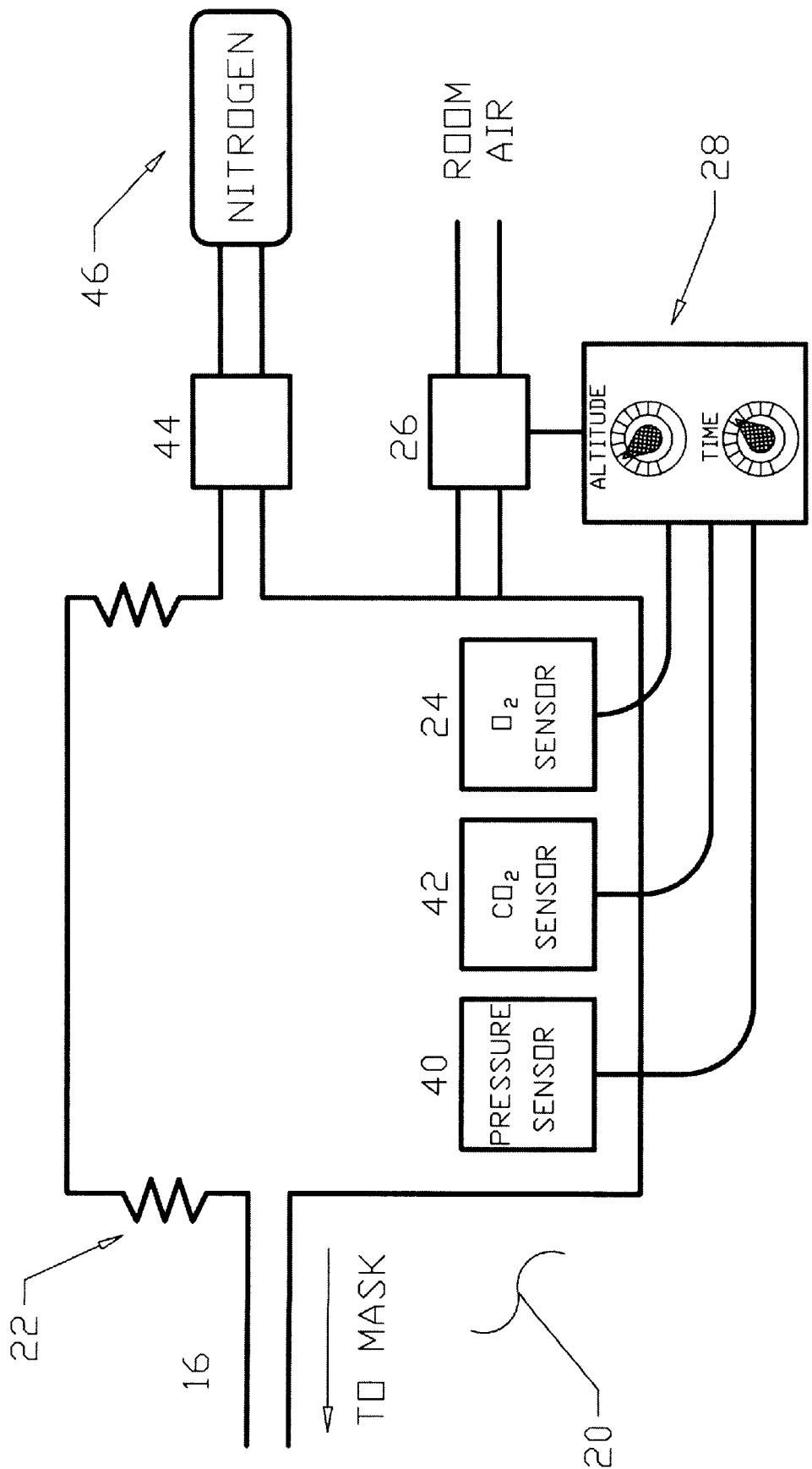
FIG. 3 shows a more complex embodiment of the device.

FIG. 3 shows a more complex embodiment of the invention which adds a pressure sensor 40 and $CO_2$ (carbon dioxide) sensor 42 which again feed into the control unit 28. This allows for the adjustment of not only the oxygen level but the $CO_2$ level. It maybe important, for some individuals, to minimize the level of $CO_2$ as high levels of $CO_2$ can interfere with breathing reflex.

A second solenoid 44 is used to allow the passage of nitrogen from a tank 46 into the chamber. This allows the reduction of oxygen levels in the chamber without merely increasing the levels of $CO_2$ as occurs with the simpler embodiment shown in FIG. 2. This further discussion of the use of this is covered in the following method discussions of FIGS. 4 and 5.

Figure 4:
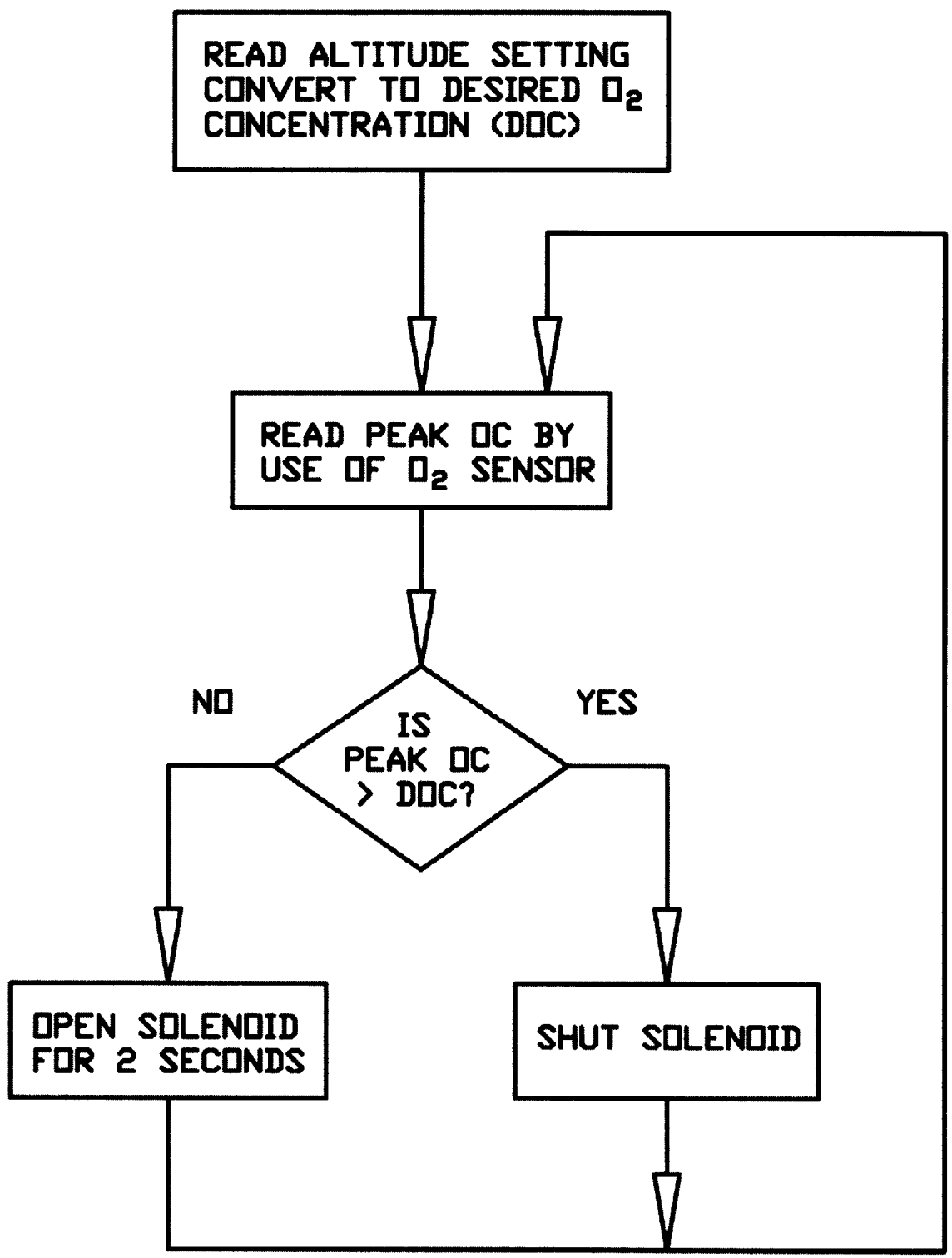
FIG. 4 shows a method of a simple embodiment.

FIG. 4 shows the method for a simple embodiment of this invention. The first step is to read the altitude setting on the control unit and to convert that to a desired oxygen level. The peak oxygen concentration is read by the $O_2$ sensor. This should occur just before inspiration as the expired air has significantly lower levels of oxygen. If the peak oxygen concentration (OC) is greater than the desired oxygen concentration (DOC) then the solenoid remains shut. This will increase the level of carbon dioxide in the gas chamber and decrease the level of oxygen.

If, in the alternative, the peak oxygen level is less than the desired oxygen concentration then the room air solenoid is open for two seconds to allow fresh air into the chamber to increase the oxygen concentration.

Figure 5:
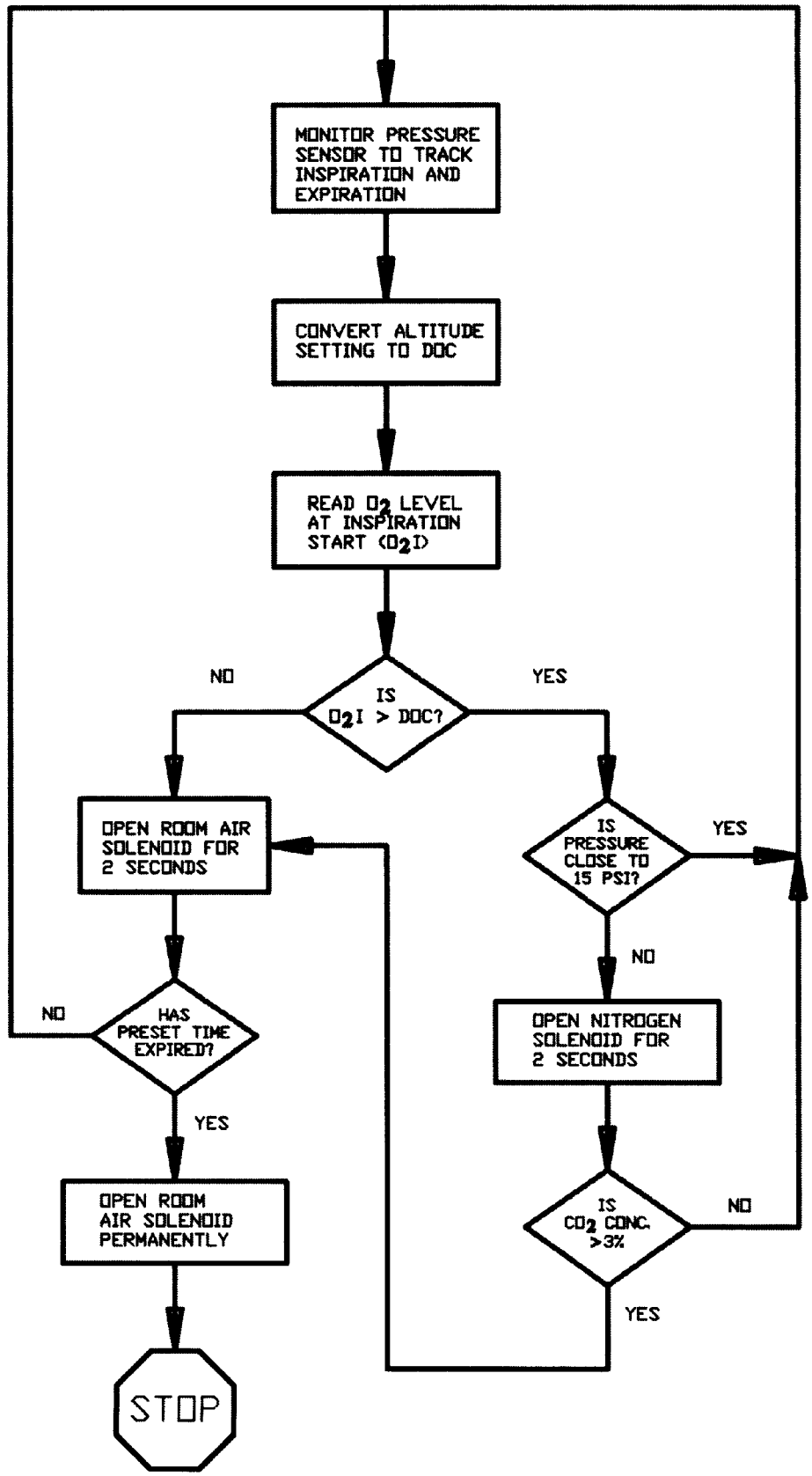
FIG. 5 shows a method for a more complex embodiment of the invention.

FIG. 5 shows a more complex embodiment of the invention. The pressure sensor in continually monitored to track inspiration and expiration. This is due to the fact that the inspiration will reduce the pressure in the tank while the expiration will increase it. Thus the control unit is continuously "aware" of the stage of breathing.

As before, the desired altitude setting is converted to a desired oxygen concentration (DOC). At the beginning of every breathing cycle (or the start of inspiration) the oxygen level is read in the exchange box. This is referred to as the "$O_2$ I". If the $O_2$ I is greater than the desired oxygen concentration then the method examines the pressure in the box. If the pressure is close to 15 PSI (pounds per square inch or normal atmospheric pressure) then this means the box has normal pressure and there is plenty of oxygen so the unit just goes back to monitoring. Eventually, breathing will lower the level of oxygen in the box. If, however, the pressure is not near normal sea level pressure then the nitrogen solenoid is opened for two seconds to increase the gas pressure. (There is no risk of great overpressure as the mask will simply allow the excess gas to leak out around the subject's mouth and nose.) After the nitrogen solenoid has been opened for two seconds then the $CO_2$ concentration is examined. If this is less than 3% then the method returns back to monitoring at the top of FIG. 5.

If, however, the $CO_2$ concentration is greater than 3% then the method opens a room air solenoid for two seconds. This allows in fresh air and will decrease the $CO_2$ concentration. The step of opening the room air solenoid for two seconds can also be reached from a negative answer to the first question. This was, "is the $O_2$ I greater than the desired oxygen concentration?" If the answer was no then it clearly needs to open the room air solenoid to let in oxygen rich air. After this step then the timer is examined. If the preset timer has expired then the room air solenoid is opened permanently to allow the subject to have comfortable normal breathing. Otherwise the system returns to its normal steps of monitoring, etc.

What is claimed is:

1. A device for acclimating an individual to high altitudes, said device comprising:
   a mask for placement on the individual's face, said mask being arranged and configured to cover at least the individual's nose and mouth;
   a gas exchange unit having a fluid inlet and a fluid outlet, said fluid outlet of said gas exchange unit being in bi-directional fluid communication with said mask;
   a first solenoid valve mounted in said gas exchange unit to control the passage of ambient air into said gas exchange unit through said fluid inlet;
   an oxygen sensor located inside said gas exchange unit, said oxygen sensor providing a first output signal which is indicative of the level of oxygen contained within said gas exchange unit; and
   a control unit connected to operate said first solenoid valve in response to said first output signal from said oxygen sensor to thereby adjust the level of oxygen contained within said gas exchange unit to simulate high altitude ambient air.

2. A device as defined in claim 1, wherein said gas exchange unit is mounted onto said mask.

3. A device as defined in claim 1, additionally comprising:
   a hose having a first end and a second end, said first end of said hose being connected to said mask such that said hose is in fluid communication with said mask, said second end of said hose being connected to said fluid outlet of said gas exchange unit such that said hose is in fluid communication with said gas exchange unit.

4. A device as defined in claim 1, additionally comprising:
   an adjustment control to cause said control unit to vary the level of oxygen contained within said gas exchange unit to different levels of oxygen simulating high altitude ambient air at a variety of different altitudes.

5. A device as defined in claim 4, wherein said adjustment control is calibrated in altitude indicia.

6. A device as defined in claim 1, wherein said control unit operates to open said first solenoid valve to increase the level of oxygen contained within said gas exchange unit and to close said first solenoid valve to decrease the level of oxygen contained within said gas exchange unit to thereby adjust the level of oxygen contained within said gas exchange unit to simulate the level of oxygen present in ambient air at a predetermined high altitude.

7. A device as defined in claim 6, wherein said control unit makes a determination to open, close, leave open, or leave closed said first solenoid valve each N seconds, said first solenoid valve being opened or being left open for the next N seconds if said control valve determines that the level of oxygen contained within said gas exchange unit is too low, said first solenoid valve being closed or being left closed for the next N seconds if said control unit determines that the level of oxygen contained within said gas exchange unit is too high.

8. A device as defined in claim 1, additionally comprising:
   a carbon dioxide sensor located inside said gas exchange unit, said carbon dioxide sensor providing a second output signal which is indicative of the level of carbon dioxide contained within said gas exchange unit;
   a pressure sensor located inside said gas exchange unit, said pressure sensor providing a third output signal which is indicative of the pressure of gas contained within said gas exchange unit;
   a source of pressurized gas; and
   a second solenoid valve mounted in said gas exchange unit to control the flow of pressurized gas from said source of pressurized gas into said gas exchange unit, whereby said control unit operates said first and second solenoid valves in response to said first, second, and third output signals to thereby adjust the pressure of gas contained within said gas exchange unit to better simulate high altitude ambient air.

9. A device as defined in claim 8, wherein said control unit operates to close said first solenoid valve to decrease the level of oxygen and increase the level of carbon dioxide contained within said gas exchange unit, and to open said first solenoid valve to increase the level of oxygen and decrease the level of carbon dioxide contained within said gas exchange unit.

10. A device as defined in claim 9, wherein said control unit makes a determination to open, close, leave open, or leave closed said first solenoid valve each N seconds, said first solenoid valve being opened or being left open for the next N seconds if said control valve determines that the level of oxygen contained within said gas exchange unit is too low and the level of carbon dioxide contained within said gas exchange unit is too high, said first solenoid valve being closed or being left closed if said control unit determines that the level of oxygen contained within said gas exchange unit is too high and the level of carbon dioxide contained within said gas exchange unit is too low.

11. A device as defined in claim 10, wherein said control unit makes a determination to open, close, leave open, or leave closed said second solenoid valve periodically, said first solenoid valve being opened or being left open for the next M seconds if said control valve determines that the level of carbon dioxide contained within said gas exchange unit is too high and the level of oxygen contained within said gas exchange unit is also too high, said second solenoid valve being closed or being left closed if said control unit determines that the level of carbon dioxide contained within said gas exchange unit is not too low.

12. A device as defined in claim 11, wherein said control unit makes a determination to open, close, leave open, or leave closed said second solenoid valve upon inspiration by the individual using the device as detected by a drop in pressure within said control unit as determined from said third output signal.

13. A device as defined in claim 1, wherein said gas exchange unit is expandable and contractible in volume such that the volume in said gas exchange unit may decrease as the individual inhales and increase as the individual exhales.

14. A device for acclimating an individual to high altitudes, said device comprising:
- a mask for placement on the individual's face, said mask being arranged and configured to cover at least the individual's nose and mouth;
- a hose having a first end and a second end, said first end of said hose being connected to said mask such that said hose is in fluid communication with said mask;
- a gas exchange unit having a fluid inlet and a fluid outlet, said second end of said hose being connected to said fluid outlet of said gas exchange unit such that said hose is in bi-directional fluid communication with said gas exchange unit;
- a first solenoid valve mounted in said gas exchange unit to control the passage of ambient air into said gas exchange unit through said fluid inlet;
- an oxygen sensor located inside said gas exchange unit, said oxygen sensor providing an output signal which is indicative of the oxygen level of gas contained within said gas exchange unit;
- a control unit connected to operate said first solenoid valve in response to said output signal from said oxygen sensor to thereby adjust the level of oxygen contained within said gas exchange unit to a level below the level of oxygen in ambient air to simulate high altitude ambient air; and
- an adjustment control to cause said control unit to vary the level of oxygen contained within said gas exchange unit to different levels of oxygen simulating high altitude ambient air at a variety of different altitudes.

15. A method for acclimating an individual to high altitudes, said device comprising:
- placing a mask on the individual's face, said mask being arranged and configured to cover at least the individual's nose and mouth, said mask being supplied with breathable gas from a gas exchange unit having a fluid inlet and a fluid outlet, said fluid outlet of said gas exchange unit being in bi-directional fluid communication with said mask;
- controlling the passage of ambient air into said gas exchange unit through a fluid inlet with a first solenoid valve mounted in said gas exchange unit;
- providing a first output signal which is indicative of the level of oxygen contained within said gas exchange unit with an oxygen sensor located inside said gas exchange unit; and
- operating said first solenoid valve with a control unit, said first solenoid valve being opened and closed in response to said first output signal from said oxygen sensor to thereby adjust the level of oxygen contained within said gas exchange unit to simulate high altitude ambient air.

16. A device as defined in claim 15, wherein said control unit is operated to open said first solenoid valve to increase the level of oxygen contained within said gas exchange unit and to close said first solenoid valve to decrease the level of oxygen contained within said gas exchange unit to thereby adjust the level of oxygen contained within said gas exchange unit to simulate the level of oxygen present in ambient air at a predetermined high altitude.

17. A device as defined in claim 15, additionally comprising:
- providing a second output signal which is indicative of the level of carbon dioxide contained within said gas exchange unit with a carbon dioxide sensor located inside said gas exchange unit;
- providing a third output signal which is indicative of the pressure of gas contained within said gas exchange unit with a pressure sensor located inside said gas exchange unit;
- providing a source of pressurized gas; and
- controlling the flow of pressurized gas from said source of pressurized gas into said gas exchange unit with a second solenoid valve mounted in said gas exchange unit, whereby said control unit operates said first and second solenoid valves in response to said first, second, and third output signals to thereby adjust the pressure of gas contained within said gas exchange unit to better simulate high altitude ambient air.

18. A device as defined in claim 15, wherein said controlling step comprises:
- operating said control unit to close said first solenoid valve to decrease the level of oxygen and increase the level of carbon dioxide contained within said gas exchange unit, and to open said first solenoid valve to increase the level of oxygen and decrease the level of carbon dioxide contained within said gas exchange unit.

19. A device as defined in claim 15, wherein said controlling step comprises:
- operating said control unit to open, close, leave open, or leave closed said second solenoid valve periodically, said first solenoid valve being opened or being left open for the next M seconds if said control valve determines that the level of carbon dioxide contained within said gas exchange unit is too high and the level of oxygen contained within said gas exchange unit is also too high, said second solenoid valve being closed or being left closed if said control unit determines that the level of carbon dioxide contained within said gas exchange unit is not too low.

* * * * *